United States Patent [19]
Shannon et al.

[11] Patent Number: 5,929,070
[45] Date of Patent: Jul. 27, 1999

[54] METHOD FOR TREATING MIGRAINE PAIN WITH OLANZAPINE

[75] Inventors: Harlan E. Shannon, Carmel, Ind.; Daniel E. Womer, Thornton, Colo.

[73] Assignee: Eli Lilly and Company, Indianapolis, Ind.

[21] Appl. No.: 08/823,457

[22] Filed: Mar. 24, 1997

Related U.S. Application Data

[60] Provisional application No. 60/014,127, Mar. 25, 1996.
[51] Int. Cl.$^6$ .................................................. A61K 31/55
[52] U.S. Cl. .............................................................. 514/220
[58] Field of Search ............................................... 514/220

[56] References Cited

U.S. PATENT DOCUMENTS 5,229,382  7/1993  Chakrabarti et al. .
5,457,101  10/1995  Greenwood et al. .

FOREIGN PATENT DOCUMENTS 582368  10/1995  European Pat. Off. .

*Primary Examiner*—William R. A. Jarvis
*Attorney, Agent, or Firm*—Arleen Palmberg

[57] ABSTRACT

The present invention provides a method for treating migraine pain comprising administering an analgesic dosage of olanzapine.

5 Claims, No Drawings

METHOD FOR TREATING MIGRAINE PAIN WITH OLANZAPINE

This application claims the benefit of U.S. Provisional Application Ser. No. 60/014,127, filed Mar. 25, 1996.

FIELD OF THE INVENTION

This invention provides a method for using 2-methyl-4-(4-methyl-1-piperazinyl)-10H-thieno[2,3-b][1,5]benzodiazepine, (hereinafter referred as "olanzapine") for the treatment of migraine pain.

BACKGROUND OF THE INVENTION

The present invention provides a method for treating migraine pain.

There is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence, and be relatively inexpensive. An especially preferred treatment for migraine pain is a compound that minimizes or eliminates the migraine pain.

Applicants have discovered that olanzapine can provide many of the characteristics of an treatment for migraine pain.

It is known that olanzapine can provide antipsychotic activity. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. Surprisingly, and in accordance with this invention, Applicants have discovered that olanzapine can be useful for the treatment of migraine pain. Olanzapine could address a long felt need for a safe and effective treatment for migraine pain.

SUMMARY OF THE INVENTION

The present invention provides a method for treating migraine pain comprising administering to a patient in need thereof, an analgesic dosage of olanzapine or a pharmaceutically acceptable salt thereof.

Detailed Description of the Invention

Olanzapine is of the formula

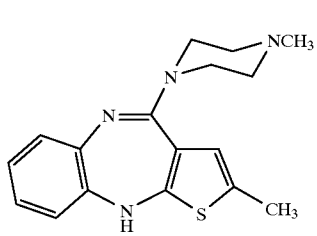

(I)

or an acid addition salt thereof.

It is especially preferred that olanzapine will be the Form II olanzapine polymorph having a typical x-ray powder diffraction pattern as represented by the following interplanar spacings:

d
10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828
3.2516
3.134
3.0848
3.0638
3.0111
2.8739
2.8102
2.7217
2.6432
2.6007

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |

-continued

| d | I/I$_1$ |
|---|---|
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper K$_a$ radiation source of wavelength, 1=1·541 Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II should contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

d 9.9463
8.5579
8.2445
6.8862
6.3787
6.2439
5.5895
5.3055
4.9815
4.8333
4.7255
4.6286
4.533
4.4624
4.2915
4.2346
4.0855
3.8254
3.7489
3.6983
3.5817
3.5064
3.3392
3.2806
3.2138
3.1118
3.0507
2.948
2.8172
2.7589
2.6597
2.6336
2.5956

A typical example of an x-ray diffraction pattern for Form I is as follows wherein d represents the interplanar spacing and I/I$_1$ represents the typical relative intensities:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper K$_a$ of wavelength 1=1.541 Å. The interplanar spacings in the column marked "d" are in Angstroms. The typical relative intensities are in the column marked "I/I$_1$".

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

Olanzapine is effective over a wide dosage range; however, it is desirable to administer a dosage that is as low as possible. For example, dosages per day of the olanzapine will normally fall within the range of about 1 mg to about 30 mg per day. However, it will be understood that the amount of the compound actually administered will be determined by a physician, in the light of the relevant circumstances including the type of acute pain to be treated, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from migraine pain, the compounds may also be administered by a variety of other routes such as the transdermal, parenteral, subcutaneous, intranasal, intramuscular and intravenous routes. Such formulations may be designed to provide delayed or controlled release using formulation techniques which are known in the art.

As used herein the term "treating" includes prophylaxis of migraine pain in a patient having a tendency to develop such pain, and the amelioration or elimination of the developed migraine pain once it has been established or alleviation of the characteristic symptoms of such migraine pain.

As used herein the term "migraine pain" shall have the meaning attributed to the condition by the skilled artisan.

The results of pharmacological studies show that olanzapine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT1C receptor. The complex pharmacological profile of the compound provides a medicament which can be useful for the treatment of migraine pain.

The dosage administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Usually, the daily dosage can be such that the active ingredient is administered at a daily dosage of from about 1 mg to about 25 mg olanzapine. Dosages of from about 1 mg to about 50 mg olanzapine may be desired.

Compositions suitable for internal administration contain from about one half (0.5) milligrams to about 500 milligrams of active ingredient per unit. In these pharmaceutical compositions, the active ingredient will ordinarily be present in an amount of from about 0.5% to about 95% by weight based on the total weight of the composition.

Typical compositions include olanzapine or a pharmaceutically acceptable acid addition salt thereof associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, olanzapine is dispensed in unit form comprising from about 1 mg to about 30 mg in a pharmaceutically acceptable carrier per unit dosage.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The compositions of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

Utility Test Methods

The unexpected migraine analgesic activity of olanzapine is evidenced by tests initially conducted on mice. Male mice are fasted for 1–2 hours and weighed. Mice weighing from about 18–22 grams at the time of testing are used for the following studies. All mice are dosed sequentially by the oral route with suspensions of classical analgesics and/or olanzapine. Doses are coded using a code unknown to the observer.

A stock suspension of olanzapine is prepared by disolving olanzapine in 10% lactic acid and bringing it up to Final volume with distilled water. The mixture may be sonicated for about 10 to about 15 seconds using an ultrasound system. All dosing suspensions are prepared by dilution of the stock suspension with distilled water. All suspensions are used within two hours of preparation.

Mouse Writhing Test

An accepted standard for detecting and comparing the analgesic activity of different classes of analgesic compounds for which there is a good correlation with human analgesic activity is the prevention of phenyl-p-benzoquinone induced writhing in mice. [H. Blumberg et al. Proc. Soc. Exp. biol. Med., 118, 763–766 (1965)].

Mice, treated with various doses of olanzapine or vehicle are injected intraperitoneally with a standard challenge dose of phenyl-p-benzoquinone 5 minutes prior to a designated observation period. The pheyl-p-benzoquinone is prepared as about 0.1 mg/ml solution in about 5% by volume of ethanol in water. The writhing dose is 1.25 mg/kg injected at a volume of about 0.25 ml/10 g. For scoring purposes a "writhe" is indicated by whole body stretching or contracting of the abdomen during an observation period beginning about five minutes after the phenyl-p-benzoquinone dose.

All ED50 values and their 95% confidence limits are determined using accepted numerical methods. For example, see W. F. Thompson, *Bacteriological Rev.*, 11, 115–145 (1947).

An accepted model for assessment of migraine pain analgesia is the Sciatic nerve ligation model as follows:

Acetic Acid-Induced Writhing

Another standard procedure for detecting and comparing the analgesic activity of different classes of analgesic drugs for which there is a good correlation with human analgesic activity is the prevention of acetic acid-induced writhing in mice. Mice are orally administered various doses of olanzapine or placebo prior to testing. The mice are then injected intraperitoneally with acetic acid (0.5% solution, 10 ml/kg) 5 min prior to a designated observation period. For scoring purposes a "writhe" is indicated by whole body stretching or contraction of the abdomen during the observation period beginning 5 min after receiving the acetic acid. Inhibition of writhing behavior is demonstrative of analgesic activity. Haubrich, D. R., Ward, S. J., Baizman, E., Bell, M. R., Bradford, J., Ferrari, R., Miller, M., Perrone, M., Pierson, A. K., Saelens, J. K. and Luttinger, D.: "Pharmacology of pravadoline: a new analgesic agent", *The Journal of Pharmacology and Experimental Therapeutics* 255 (1990) 511–522.

It is believed that neurogenic meningeal extravasation leads to the pain of migraine; therefore, the binding affinity of olanzapine to serotonin receptors, which are associated with this condition, is measured first using standard procedures. For example, the ability of a compound to bind to the $5\text{-HT}_{1F}$ receptor subtype is performed essentially as described in N. Adham, et al., *Proceedings of the National Academy of Sciences* (USA), 90, 408–412 (1993). For comparison purposes, the binding affinities of olanzapine to other serotonin receptors is determined essentially as described below except that different cloned receptors are employed in place of the $5\text{-HT}_{1F}$ receptor clone employed therein.

Membrane Preparation

Membranes are prepared from transfected Ltk- cells which are grown to 100% confluency. The cells are washed twice with phosphate-buffered saline, scraped from the culture dishes into 5 mL of ice-cold phosphate-buffered saline, and centrifuged at 200 x g for 5 minutes at 4° C. The pellet is resuspended in 2.5 mL of ice-cold Tris buffer (20 mM Tris HCl, pH=7.4 at 23° C., 5 mM EDTA) and homogenized with a Wheaton tissue grinder. The lysate is subsequently centrifuged at 200 x g for 5 minutes at 4° C. to pellet large fragments which are discarded. The supernatant is collected and centrifuged at 40,000 x g for 20 minutes at 4° C. The pellet resulting from this centrifugation is washed once in ice-cold Tris wash buffer and resuspended in a final buffer containing 50 mM Tris HCl and 0.5 mM EDTA, pH=7.4 at 23° C. Membrane preparations are kept on ice and utilized within two hours for the radioligand binding assays. Protein concentrations are determined by the method of Bradford (*Anal. Biochem.*, 72, 248–254 (1976)).

Radioligand Binding

[$^3$H 5-HT] binding is performed using slight modifications of the $5\text{-HT}_{1D}$ assay conditions reported by Herrick-Davis and Titeler (*J. Neurochem.*, 50, 1624–1631 (1988)) with the omission of masking ligands. Radioligand binding studies are achieved at 37° C. in a total volume of 250 mL of buffer (50 mM Tris, 10 mM $MgCl_2$, 0.2 mM EDTA, 10 mM pargyline, 0.1% ascorbate, pH=7.4 at 37° C.) in 96 well microtiter plates. Saturation studies are conducted using [$^3$H]5-HT at 12 different concentrations ranging from 0.5 nM to 100 nM. Displacement studies are performed using 4.5–5.5 nM [$^3$H]5-HT. The binding profile of drugs in competition experiments is accomplished using 10–12 concentrations of compound. Incubation times are 30 minutes for both saturation and displacement studies based upon initial investigations which determine equilibrium binding conditions. Nonspecific binding is defined in the presence of 10 mM 5-HT. Binding is initiated by the addition of 50 mL membrane homogenates (10–20 mg). The reaction is terminated by rapid filtration through presoaked (0.5% poylethyleneimine) filters using 48R Brandel Cell Harvester (Gaithersburg, Md.). Subsequently, filters are washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity is measured using a Beckman LS 5000TA liquid scintillation counter. The efficiency of counting of [$^3$H]5-HT averages between 45–50%. Binding data are analyzed by computer-assisted nonlinear regression analysis (Accufit and Accucomp, Lunden Software, Chagrin Falls, Ohio). $IC_{50}$ values are converted to $K_i$ values using the Cheng-Prusoff equation (*Biochem. Pharmacol.*, 22, 3099–3108 (1973).

As was reported by R. L. Weinshank, et al., WO93/14201, the $5\text{-HT}_{1F}$ receptor is functionally coupled to a G-protein as measured by the ability of serotonin and serotonergic drugs to inhibit forskolin stimulated cAMP production in NIH3T3 cells transfected with the $5\text{-HT}_{1F}$ receptor. Adenylate cyclase activity is determined using standard techniques. A maximal effect is achieved by serotonin. An $E_{max}$ is determined by dividing the inhibition of olanzapine by the maximal effect and determining a percent inhibition. (N. Adham, et al., supra,; R. L. Weinshank, et al., *Proceedings of the National Academy of Sciences* (USA), 89,3630–3634 (1992)), and the references cited therein.

Measurement of cAMP Formation

Transfected NIH3T3 cells (estimated Bmax from one point competition studies=488 fmol/mg of protein) are incubated in DMEM, 5 mM theophylline, 10 mM HEPES (4-[2-hydroxyethyl]-1-piperazineethanesulfonic acid) and 10 mM pargyline for 20 minutes at 37° C., 5% $CO_2$. Drug concentration-effect curves are then conducted by adding 6 different final concentrations of drug, followed immediately by the addition of forskolin (10 mM). Subsequently, the cells are incubated for an additional 10 minutes at 37° C., 5% $CO_2$. The medium is aspirated and the reaction is stopped by the addition of 100 mM HCl. To demonstrate competitive antagonism, a concentration-response curve for 5-HT is measured in parallel, using a fixed dose of methiothepin (0.32 mM). The plates are stored at 4° C. for 15 minutes and then centrifuged for 5 minutes at 500 x g to pellet cellular debris, and the supernatant is aliquoted and stored at –20° C. before assessment of cAMP formation by radioimmunoassay (cAMP radioimmunoassay kit; Advanced Magnetics, Cambridge, Mass.). Radioactivity is quantified using a Packard COBRA Auto Gamma counter, equipped with data reduction software.

The following test is performed to determine the ability of the panel compounds to inhibit protein extravasation which is a functional assay for the neuronal mechanism of migraine.

Protein Extravasation Assay

Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posterially, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the ends (Rhodes Medical Systems, Inc.), are lowered through the holes in both hemispheres to a depth of 9 mm (rats) or 10.5 mm (guinea pigs) from dura.

The femoral vein is exposed and a dose of olanzapine is injected intravenously (1 mL/kg). Approximately 7 minutes later, a 50 mg/kg dose of Evans Blue, a fluorescent dye, is also injected intravenously. The Evans Blue complexes with proteins in the blood and function as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are killed and exsanguinated with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monchromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve is generated and the dose that inhibited the extravasation by 50% ($ID_{50}$) is approximated.

To determine if a relationship existed between the binding affinity to each of the $5-HT_{1Da}$, $5-HT_{1Db}$, $5-HT_{1E}$ and $5-HT_{1F}$ receptors and neuronal protein extravasation, binding affinity for each receptor subtype is plotted against their $ID_{50}$ in the protein extravasation model. A linear regression analysis is performed on each set of data and a correlation factor, $R^2$, is then calculated.

The following assay to measures olanzapine's ability to mediate vasoconstriction in the rabbit saphenous vein.

Rabbit Saphenous Vein Contraction

Male New Zealand White rabbits (3–6 lbs) (Hazleton, Kalamazoo, Mich.) are sacrificed by a lethal dose of sodium pentobarbital (325 mg) injected into the ear vein. Tissues are dissected free of connective tissue, cannulated in situ with polyethylene tubing (PE50, outside diameter=0.97 mm) and placed in petri dishes containing Kreb's bicarbonate buffer (described infra). The tips of two 30-gauge stainless steel hypodermic needles bent into an L-shape are slipped into the polyetylene tubing. Vessels are gently pushed from the cannula onto the needles. The needles are then separated so that the lower one was attached with thread to a stationary glass rod and the upper one was tied with thread to the transducer.

Tissues are mounted in organ baths containing 10 mL of modified Krebs' solution of the following composition: 118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$. Tissue bath solutions are maintained at 37° C. and aerated with 95% $O_2$ and 5% $CO_2$. An initial optimum resting force of 1 gm was applied to the saphenous vein. Isometric contractions are recorded as changes in grams of force on a Beckman Dynograph with Statham UC-3 transducers and microscale accessory attachments. Tissues are allowed to equilibrate 1 to 2 hours before exposure to drugs. Cumulative agonist concentration-response curves are generated in tissues and no tissue is used to generate more than two agonist concentration-response curves. All results are expressed as a mean $EC_{50}$ and the maximal response is expressed as a percentage of the response to 67 mM KCl administered initially in each tissue.

This vasoconstriction assay measures two important parameters, saphenous vein contraction ($EC_{50}$) and maximal contraction as a % maximal KCl response. The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The % maximal KCl contraction is the ratio of the maximal response that the specific compound is capable of mediating divided by the maximal response that the tissue can produce.

A measure of this specificity is the ratio of vasoconstriction to efficacy in inhibition of neuronal protein extravasation. This ratio, defined as the Specificity Index where:

$$\text{Specificity Index} = \frac{\text{Corrected Vasoconstriction } EC_{50}(M)}{\text{Extravasation } ID_{50}(\text{mMol}/\text{kg})}$$

To correct the $EC_{50}$ values for saphenous vein contraction so that the maximal contraction relative to KCl for each individual compound can be taken into consideration, the vasoconstriction $ID_{50}$ value is divided by the % maximum KCl contraction to give the "corrected vasoconstriction $EC_{50}$ (M)".

While a compound or composition with a Specificity Index greater than 1 is useful for the method of this invention, larger values for the Specificity Index are preferred. A larger Specificity Index indicates greater specificity for efficacy in inhibition of neuronal protein extravasation over vasoconstriction.

In summary, the usefulness of a compound or a composition in a method for the treatment of the pain of migraine and associated disorders without substantial side effects caused by vasoconstriction is determined by its Specificity Index. The Specificity Index is the ratio of vasoconstriction to efficacy in inhibition of neuronal protein extravasation.

Measurement of the ability of a compound or composition to inhibit neuronal protein extravasation is a functional assay for the physiological events leading to migraine pain.

Surprisingly, such experiments suggest that olanzapine can provide a significant migraine pain analgesic effect.

Clinical Observations

A double-blind multicenter clinical trial is designed to assess the safety and efficacy of olanzapine. Patients are randomized to olanzapine or placebo. Patients are monitored for perception of pain using standard methods.

Such clinical trial results suggest that olanzapine can be a relatively safe compound for the treatment of migraine pain.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

Preparation 1

Technical Grade Olanzapine

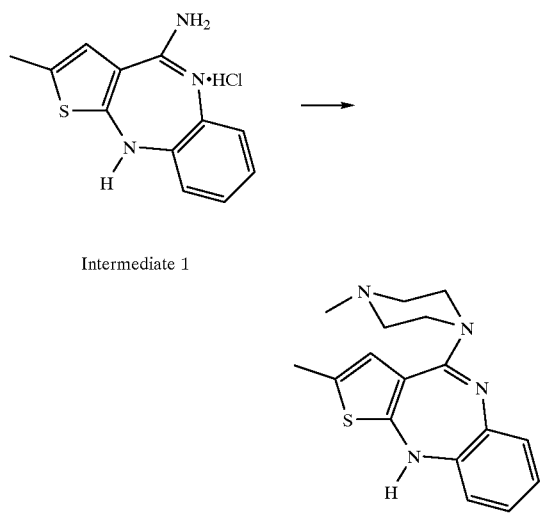

Intermediate 1

In a suitable three neck flask the following was added:
Dimethylsulfoxide (analytical): 6 volumes
Intermediate 1 : 75 g
N-Methylpiperazine (reagent) : 6 equivalents
Intermediate 1 can be prepared using methods known to the skilled artisan. For example, the preparation of the Intermediate 1 is taught in the '382 patent. A sub-surface nitrogen sparge line was added to remove the ammonia formed during the reaction. The reaction was heated to 120° C. and maintained at that temperature throughout the duration of the reaction. The reactions were followed by HPLC until [2] 5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

Preparation 2

Form II Olanzapine Polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L) . The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency $\geq 97\%$, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution . The operation was performed in a perforated coating pan.

Coating of Core Tablets

Color Mixture White (hydroxypropyl methylcellulose, polyethylene glycol, polysorbate 80, and titanium dioxide)

was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A method for treating migraine pain in a mammal in need of such treatment, comprising administering an effective amount of olanzapine to the mammal.

2. A method of claim 1 wherein the mammal is a human.

3. A method of claim 2 wherein olanzapine is Form II olanzapine polymorph.

4. A method of claim 2 wherein the effective amount of olanzapine is from about 5 mg to about 30 mg per day.

5. A method of claim 4 wherein the effective amount of olanzapine is from about 5 mg to about 25 mg per day.

* * * * *